United States Patent
Kroll et al.

(10) Patent No.: US 6,411,844 B1
(45) Date of Patent: Jun. 25, 2002

(54) FAST RECOVERY SENSOR AMPLIFIER CIRCUIT FOR IMPLANTABLE MEDICAL DEVICE

(75) Inventors: Mark W Kroll, Simi Valley, CA (US); Steve Chang, West Linn, OR (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/420,925

(22) Filed: Oct. 19, 1999

(51) Int. Cl.$^7$ ................................................ A61N 1/39
(52) U.S. Cl. ............................ 607/5; 607/63; 125/908
(58) Field of Search ..................... 607/5, 9, 13, 63; 128/908

(56) References Cited

U.S. PATENT DOCUMENTS

| | | | |
|---|---|---|---|
| 4,406,286 A | 9/1983 | Stein | 128/419 |
| 4,543,956 A | 10/1985 | Herscovici | 128/419 |
| 4,637,397 A | 1/1987 | Jones et al. | 128/419 |
| 4,809,697 A | 3/1989 | Causey, III et al. | 128/419 |
| 4,903,700 A | 2/1990 | Whigham et al. | 128/419 |
| 4,944,299 A | 7/1990 | Silvian | 128/419 |
| 5,257,621 A | 11/1993 | Bary et al. | 607/5 |
| 5,330,512 A | 7/1994 | Hauck et al. | 607/28 |
| 5,507,781 A | 4/1996 | Kroll et al. | 607/7 |
| 5,522,853 A | 6/1996 | Kroll | 607/5 |
| 5,601,608 A * | 2/1997 | Mouchawar | 607/13 |
| 5,741,312 A | 4/1998 | Vonk et al. | 607/28 |
| 5,913,877 A | 6/1999 | Kroll et al. | 607/5 |
| 5,964,787 A | 10/1999 | Kerver et al. | 607/9 |
| 6,002,962 A | 12/1999 | Huang et al. | 607/5 |
| 6,067,472 A | 5/2000 | Vonk et al. | 607/28 |

* cited by examiner

Primary Examiner—Jeffrey R. Jastrzab

(57) ABSTRACT

Therapeutic shocks generated by implantable cardiac stimulators, such as implantable cardioverter-defibrillator devices, may result in residual charges being deposited on the defibrillation electrodes and/or polarization of the tissues surrounding the defibrillation electrodes. These parasitic charges and polarization may mask a possible ventricular fibrillation of the heart following the application of the therapeutic shocks because such a ventricular fibrillation is characterized by intrinsic signals of very small amplitudes. A small duration pulse is applied to the electrodes right after a therapeutic shock. In addition, or alternatively, the electrodes can also be shorted together to dissipate the parasitic charges and the polarization of the tissue. As a result, a ventricular fibrillation can be detected earlier than in previous cardiac stimulators.

8 Claims, 5 Drawing Sheets

FAST RECOVERY SENSOR AMPLIFIER CIRCUIT FOR IMPLANTABLE MEDICAL DEVICE

FIELD OF THE INVENTION

This invention pertains to an implantable medical device, and more particularly, to an implantable cardioverter-defibrillator (ICD), which senses a dangerous cardiac arrhythmia and, in response, provides therapy to a patient's heart to revert it to a normal sinus rhythm. More particularly, this invention pertains to an ICD in which a depolarization pulse is applied after a defibrillation shock, and/or the electrodes used to deliver the defibrillation shock are shorted together for a brief time period, to discharge any residual charges, thereby insuring that intrinsic cardiac signals indicative of fibrillation are not masked.

BACKGROUND OF THE INVENTION

As used herein, the term "arrhythmia" refers to any abnormal heart rhythm that may be dangerous to the patient and specifically includes fibrillation, atrial tachycardias, supraventricular tachycardias (SVT), ventricular tachycardias (VT), ventricular fibrillation and flutter (VF). As further used-herein, the term "therapy" refers to any means used by the ICD device to restore normal heart rhythm, such as defibrillation, cardioversion, and antitachycardia pacing. The term "cardioverter" refers to a device capable of providing defibrillation therapy, cardioversion therapy, or both.

Typically, defibrillation therapy consists of the application to cardiac tissue of one or more electrical shocks of considerable amplitude and duration. In cases where a first defibrillation shock is not successful, a second shock having much smaller amplitude applied within about 1–2 seconds after the first shock may suffice to revert the heart to normal sinus rhythm. It is desirable to apply a subsequent defibrillation shock as soon as it is discovered that the heart has not reverted despite earlier attempts.

However, such therapy immediately after the delivery of a defibrillation shock has not always been possible because it may not be possible to sense the on-going arrhythmia (including VF) for many seconds after a defibrillation shock is applied. More particularly, until now such early therapy additional (e.g., second-shock) could not be applied because the first defibrillation shock results in a build-up of residual charge on the electrodes and a local polarization of the tissues which would dissipate only after about 10 seconds. This may mask any low amplitude VF, and necessarily lead to a delay in the application of another shock.

SUMMARY OF THE INVENTION

In its broadest sense, the present invention pertains to an ICD wherein a two-step process is executed after the administration of high energy level therapy such as a defibrillation shock consisting of one or more high amplitude pulses. The process consists of first applying a relatively short duration and low amplitude pulse, preferably having a polarity opposite to that of the last pulse of the therapy, to depolarize the electrodes thereby dissipating any residual or parasitic charges therein. Following this short duration pulse, the electrodes used to apply the therapy are momentarily shorted together to discharge any remaining residual charges.

In a particularly advantageous arrangement, a multiphasic shock is generated by a circuit that includes a capacitor charged to a preselected voltage of at least 100V and then discharged through a set of electronic switches arranged in a bridge-like fashion. In this arrangement, the short duration pulse is generated by applying a charge from the capacitor to the electrodes using the same switches that control or steer the therapy shock. After the short duration pulse, additional switches are used to short the electrodes together.

Advantageously, the electrodes may also be shorted to the conductive case of the ICD, especially in arrangements where the conductive case acts as anelectrode as well.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
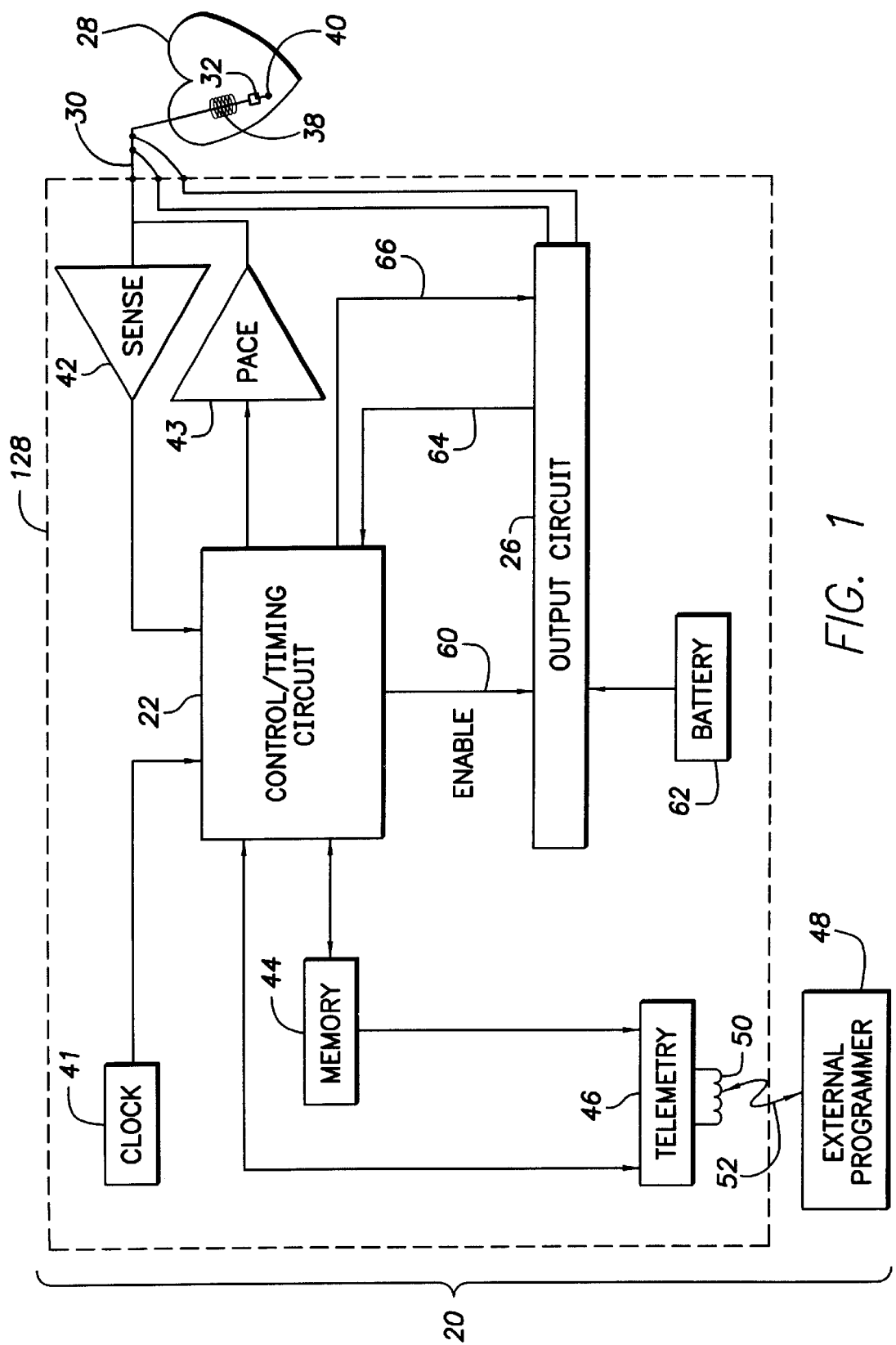
FIG. 1 shows a simplified functional block diagram of an implantable cardioverter-defibrillator (ICD)

As indicated above, the present invention may be used with various types of implantable medical devices, including an implantable cardioverter-defibrillator (ICD). To better understand the invention, it will first be helpful to provide a description of the basic functions performed by the implantable medical device with which the invention is used, e.g., an ICD device. To that end, reference is first made to FIG. 1, where there is shown a simplified functional lock diagram of an ICD 20. It should be noted that in some instances the functions of an ICD may be combined with the functions of a pacemaker within the same medical device. A primary function of an ICD device is to detect the occurrence of an arrhythmia, and to automatically apply an appropriate electrical defibrillation shock to the heart to terminate the arrhythmia, as discussed more fully below. Toward this end, the ICD 20 includes a microprocessor-based control and timing circuit 22 (hereafter a "control/timing" circuit 22) that controls an output circuit 26. The output circuit 26 generates output electrical stimulation pulses of moderate or high energy (cardioversion pulses or defibrillation shocks), e.g., electrical pulses having energies of from 1 to 5 joules (moderate) or 6 to 40 joules (high), as controlled by the control/timing circuit 22. Such moderate or high energy shocks are applied to the patient's heart 28 through a lead 30 coupled to two suitable defibrillator electrodes 38 and 128 implanted in the heart 28. While only one lead and two electrodes are shown in FIG. 1, it is to be understood that additional defibrillation leads and electrodes may be used as desired or needed in order to efficiently and effectively apply to the patient's heart 28, the shock generated by the output circuit 26.

The ICD 20, disposed in a conductive case 128, includes sense amplifier 42, coupled to electrodes 32 or 38 and 40 via lead 30. The sense amplifier 42 amplifies the electrical signal indicative of the activity of the heart 28 that appears on the electrodes 32 or 38 and 40. That is, as is known in the art, an R-wave occurs upon the depolarization, and hence contraction, of ventricular tissue; and a P-wave occurs upon the depolarization, and hence contraction, of atrial tissue. Thus, by sensing electrical signals indicative of R-waves and/or P-waves, amplifying such signals through the sense amplifier 42, and providing such amplified signals to the control/timing circuit 22, the control/timing circuit 22 is able to determine the rate and regularity of the patient's heartbeat. Such data provides the basis for the control/timing circuit 22 to determine whether heart 28 is malfunctioning. (As will be understood, if both P-waves and R-waves are to be sensed, two leads and sense amplifiers must be used.)

The control/timing circuit 22 further has a memory 44 coupled thereto, wherein the operating parameters used by the control/timing circuit 22 are stored. Such operating parameters define, for example, a therapy to be applied to treat the heart 28, including a plurality of shocks, including the amplitude of each shock to be delivered to the heart 28 within each defined tier of therapy.

Advantageously, the operating parameters of the ICD 20 may be non-invasively programmed into the memory 44 through a telemetry circuit 46, in telecommunications contact with an external programmer 48 through a coupling coil 50. The coupling coil 50 may serve as an antenna for establishing a radio frequency (rf) communications link 52 with the external programmer 48; or the coil 50 may serve as a means for inductively coupling data to and from the telemetry circuit 46 from and to the external programmer 48, as is known in the art. See, e.g., U.S. Pat. Nos. 4,809,697 (Causey, III et al.) and U.S. Pat. No. 4,944,299 (Silvian), incorporated herein by reference. Further, such telemetry circuit 46 advantageously allows status information relating to the operation of the ICD 20, as contained in the control/timing circuit 22 or memory 44, to be sent to the external programmer 48 through the established (rf) communications link 52.

The control/timing circuit 22 includes appropriate processing and logic circuits for analyzing the output signals of the sense amplifier 42 and determining if such signals indicate the presence of an arrhythmia. Typically, the control/timing circuit 22 is based on a microprocessor, or similar processing circuit, which includes the ability to process or monitor input signals (data) in a prescribed manner, e.g., as controlled by program code stored in a designated area or block of the memory 44. The use, design, and operation of microprocessor-based control circuits including the control/timing 22 circuit to perform timing and data analysis functions is known in the art and therefore need not be described in detail here.

As previously mentioned, a problem associated with the application of defibrillation therapy is that whenever a shock is applied, the tissue around the electrodes 38 and 40 becomes polarized. Moreover, the shock results in a build up of a residual charge, generally of about 1 volt, across the defibrillator leads that takes several seconds to dissipate.

The problem with the build up of charge on the defibrillator electrodes is that it masks detection of a possible ventricular fibrillation. More particularly, ventricular fibrillation is characterized by a signal in the order of 1 mV which may set in as early as 100 ms after a defibrillation shock. In the presence of any remaining charge on the electrodes, fibrillation is difficult to sense. Hence, in prior art ICDs the sensing of intrinsic cardiac activity was delayed for a period sufficient to ensure that the remaining charge had dissipated.

This invention resolves the above-described limitation by applying at the end of a typical defibrillation shock a short duration pulse having a relatively small amplitude and duration. For example, referring to FIG. 2, a typical defibrillation shock is shown having two pulses: a positive pulse 100 and a negative pulse 102. Following the negative pulse 102, an additional short duration pulse 104 is applied. While the duration of pulses 100 and 102 is in the order of 6 ms, the pulse 104 is much shorter, i.e., in the order 1 ms or less. Similarly, while the peak amplitudes of the pulses 100, 102 are about 750 and 300 volts respectively, the peak amplitude of short duration pulse 104 is about 100 volts. Since the pulse 104 is positive, it provides for the discharge of any residual charges on the leads used to apply the defibrillation shock.

Following short duration pulse 104, the defibrillation electrodes are shorted together to further dissipate any residual charges. We have found that a positive short duration pulse on one of the cardiac electrodes is more effective than a negative pulse on the case of the ICD, if the case is used as one of the electrodes.

Figure 3:
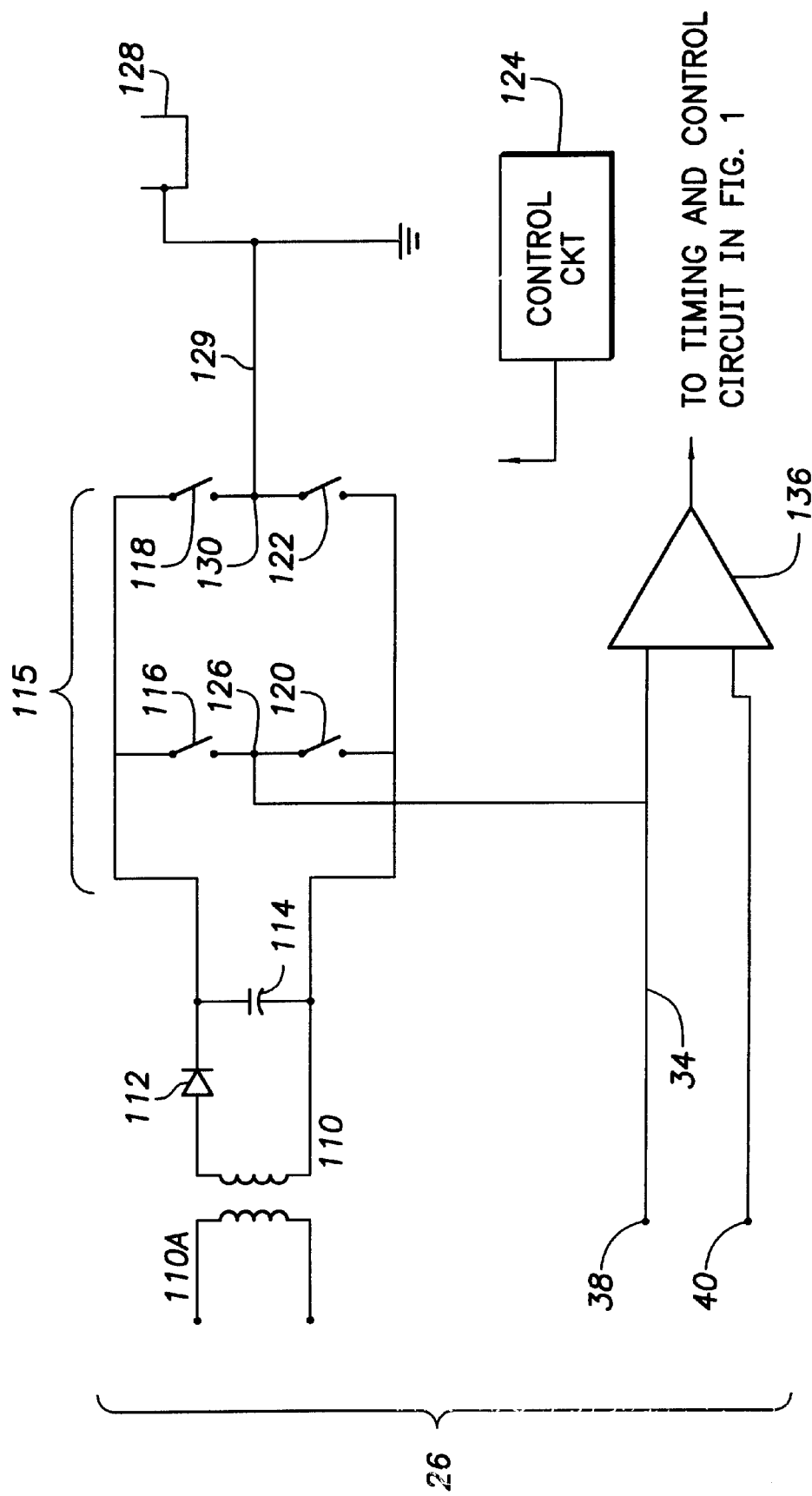
FIG. 3 shows a prior art circuit for generating defibrillation shocks and for sensing an electrogram signal.

FIG. 3 shows a schematic of a typical prior art output circuit 26. In this figure, the output circuit 26 includes a secondary coil 110 which cooperates with a primary coil 110A to define a transformer. The primary coil receives pulses from a power supply, not shown, which results in a charging voltage in the secondary coil 110. This voltage is applied through a diode 112 to charge a capacitor 114.

A switching bridge 115 formed of four switches 116, 118, 120, 122 is also provided in the output circuit 26. These switches 116–122 are electronic switches whose states (open or closed) are determined by a control circuit 124. One node 126 of bridge 115 is connected to the electrode 38 while the other node 130 is connected to grounded housing 128 of the ICD 20 by a wire 129.

Figure 2:
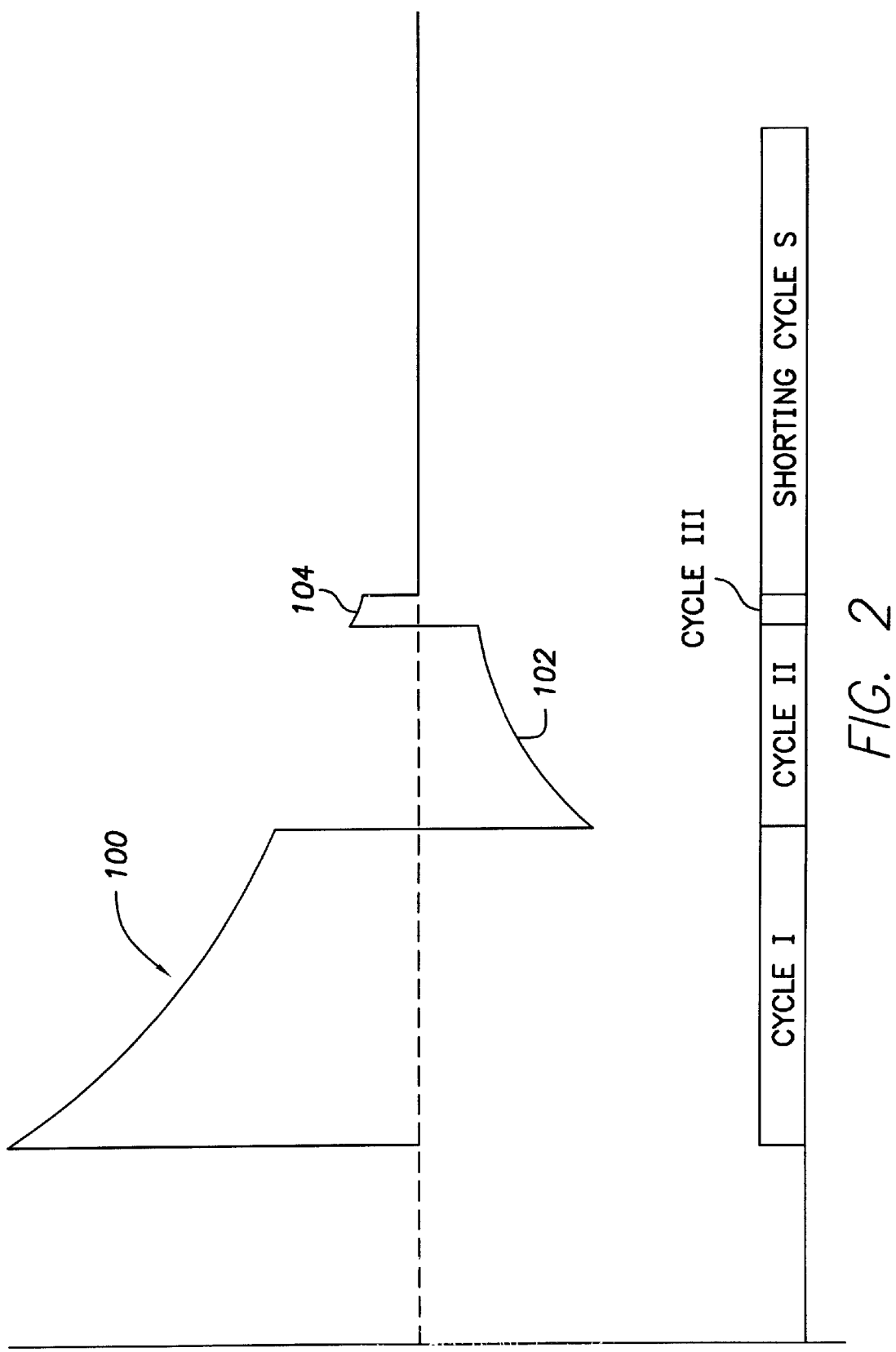
FIG. 2 shows a multiphasic defibrillation shock applied to the heart of a patient to revert the heart to normal sinus rhythm, to depolarize the defibrillation electrodes, and to dissipate charges within the cardiac tissues.

The circuit of FIG. 3 can be used to generate a defibrillation shock between the electrode 38 and the case 128, the stimulation shock being composed of the two pulses 100 and 102 shown in FIG. 2, by selectively opening and closing switches 116–122. The cardiac activity before and after the shock is monitored through an amplifier 136 which senses the voltage between the electrode 38 and, the electrode 40.

The sequence of opening and closing the switches 116–122 is described in detail below.

Figure 4:
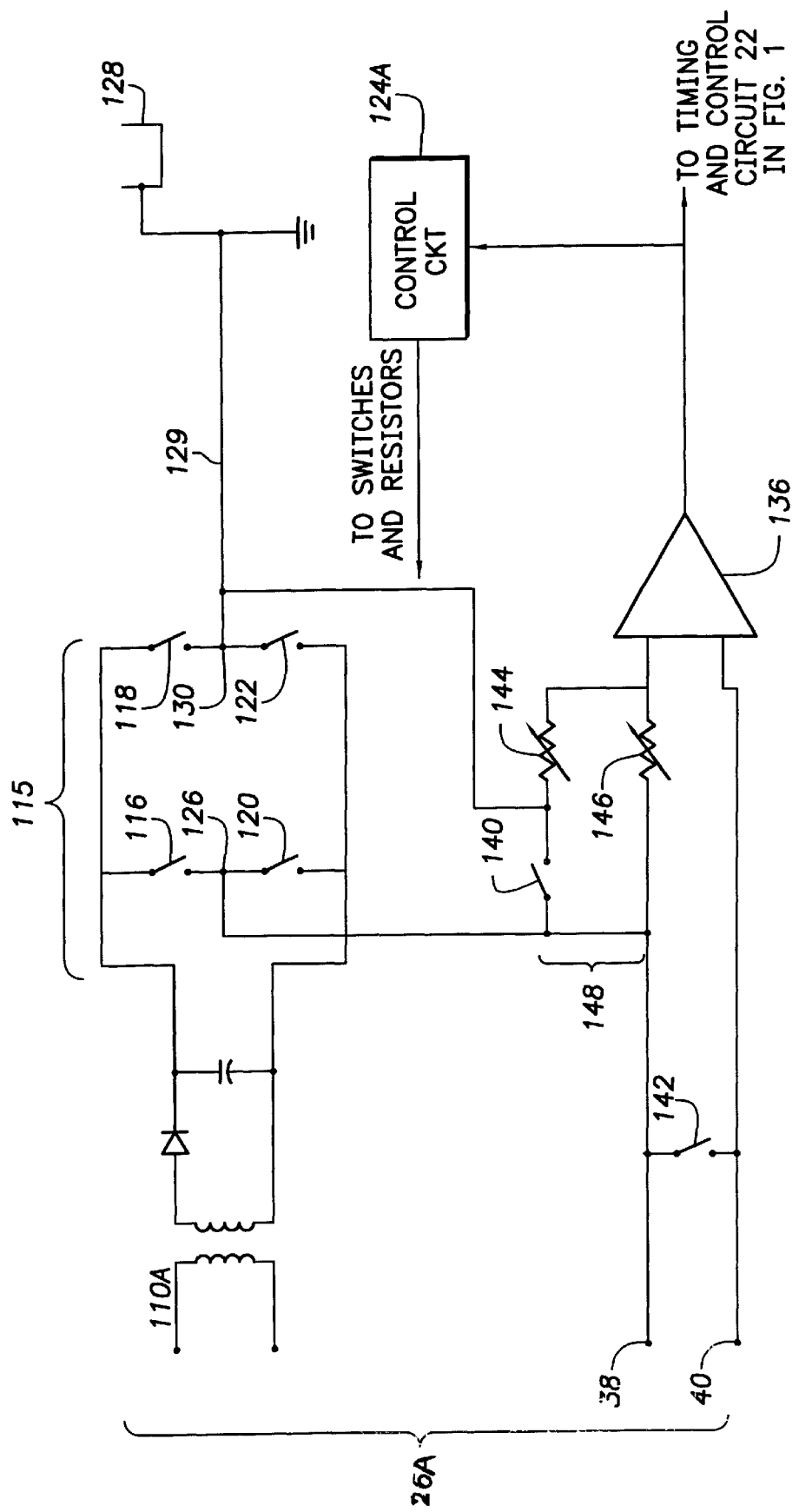
FIG. 4 shows a circuit for generating multiphasic shocks and for shorting the defibrillation electrodes together in accordance with the present invention.

The circuit of FIG. 3 is easily modified to generate the pulses of the subject invention, as shown in FIG. 4. In FIG. 4, control circuit 124A operates switches 118–122, thereby generating pulses 100, 102 to be applied to the electrodes. However, additional control signals are also generated by control circuit 124A to cause the short duration pulse 104, shown in FIG. 2, to be applied to the electrode 38, as explained in detail below. Output circuit 26A of FIG. 4 includes all the components of output circuit 26 of FIG. 3, and in addition also includes switches 140, 142 and variable resistors 144, 146. Switch 140, when closed, grounds electrode 38 to case 128 while switch 142, when closed, shorts electrodes 38 and 40 together.

Amplifier 136 measures the intrinsic voltage generated between electrodes 38 and 40 and transmits the value of this intrinsic voltage to the control circuit 124A as well as to the timing and control circuit 22 (in FIG. 1). The control circuit 124A senses this value after a defibrillation shock signal. The control circuit 124A will seek to "drive" the voltage down to an average value of zero. The polarization is typically negative on the electrode 38. But the polarization on the housing 128 will, naturally, be opposite. By adjusting the relative values of input weighting resistors 144 and 146, the control circuit 124A can find a neutral (zero offset voltage) reference for amplifier 136. Of course, the electrogram signal is an AC signal superimposed over the decaying polarization signal. Thus, the feedback speed of control circuit 124A must be limited so that it does not cancel out the electrogram signal desired at the output of amplifier 136.

In normal operation (i.e., not post-shock), resistor 144 is at an essentially infinite value so that the sensing reference is purely electrode 38.

The circuit 26A in FIG. 4 best describes the invention in use with the so-called "integrated" bipolar sensing. With this scheme, the right ventricular (RV) coil senses both as shocking electrode (hence, the connection to node 126) and as the sensing reference electrodes. The dual purpose role is allowed by the jumper 148 which may be in the ICD, but most typically in the lead assembly itself.

Another popular lead system has the "true bipolar" sensing scheme. In this case, there is no jumper 148 and sensing-reference electrode is a distinct ring (e.g., electrode 32) placed between the RV coil 38 and the tip electrode 40. The operation of the invention with the true bipolar scheme would preferably be identical to that described earlier for the dedicated bipolar lead system. As an alternate embodiment, a third variable resistor (in addition to 144 and 146) could be used to connect the RV coil electrode (node 126) to the upper input of amplifier 136. In this way, control circuit 124A takes advantage of the existence of three choices for the reference electrode. By suitably balancing the three, it is most likely to rapidly find a neutral reference.

Figure 5:
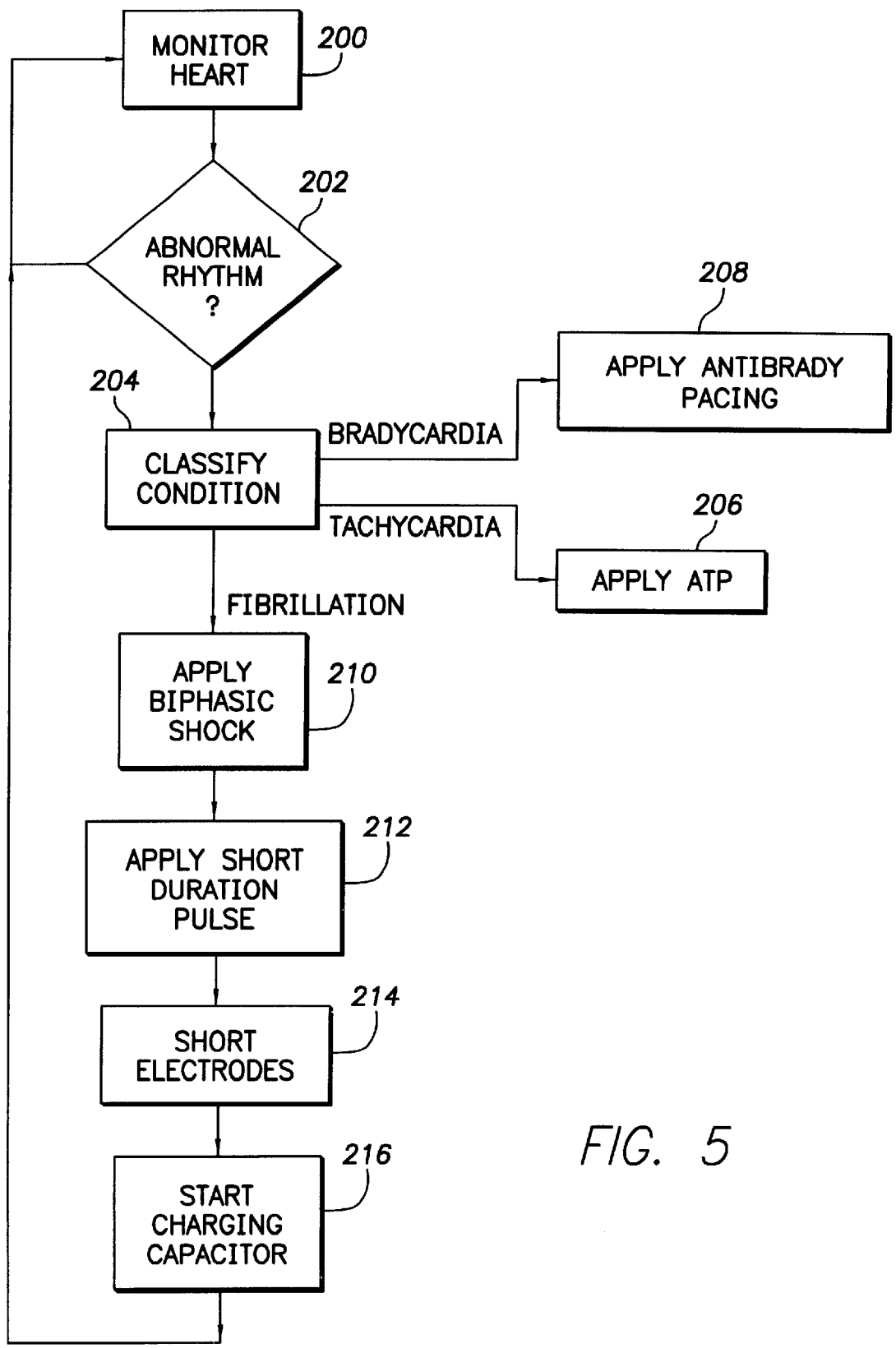
FIG. 5 shows a flowchart for the operation of the ICD of FIGS. 1 and 4.

The operation of the ICD 20 of FIG. 1 and more specifically the output circuit 26A of FIG. 4 will now be described in conjunction with the flow chart of FIG. 5.

The heart 28 is monitored at step 200 to determine and classify its condition. At step 202 the control/timing circuit 22 makes a decision as to whether the heart 28 is exhibiting an abnormal rhythm. If an abnormal rhythm is detected, then at step 204 the condition of the heart is classified as either fibrillation, tachycardia or bradycardia. Procedures and algorithms for making this determination are described, for example, in U.S. Pat. No. 5,257,621 (Bardy), incorporated herein by reference.

In the case of a low rate tachycardia, antitachycardia pacing therapy (ATP) is applied at step 206. In the case of a bradycardia, antibradycardia therapy is applied at step 208.

If fibrillation is identified at step 204, then a defibrillation therapy is applied as follows. At step 210, a biphasic defibrillation shock comprising two pulses 100, 102 as shown in FIG. 2 is applied between electrodes 38 and 128, by sending a command signal from the control timing control circuit 22 to the output circuit 26A. In response, the output circuit 26A defines the four sequential cycles which are identified as cycle I, cycle II, cycle III, and a shorting cycle S, as illustrated in FIG. 2.

During cycle I, switches 116 and 122 close causing the capacitor 114 to discharge and apply positive pulse 100 between electrodes 38 and 128.

At the end of cycle I, the output circuit 26A switches to cycle II by opening switches 116, 122 and closing switches 118, 120. This causes the capacitor 114 to continue to discharge at approximately the same rate as in cycle I but the polarity of the resulting pulse 102 has the opposite, or negative, polarity with respect to pulse 100 as shown in FIG. 2. The end of cycle II as determined by output circuit 26A constitutes the end of the standard biphasic defibrillation shock. Next, at step 212, the short duration pulse 104 is applied between the electrodes 38 and 128. This short duration pulse is used to dissipate residual or parasitic charges on the electrodes, or the polarization of the tissues, around the electrodes. Importantly, this short duration pulse has a low amplitude so that it does not stimulate the cardiac tissues. This is accomplished during cycle III by output circuit 26A which opens switches 120 and 118, and once again closes switches 116, 122.

At step 214, output circuit 26A initiates the shorting cycle S. Switches 116, 122 are opened, and switches 140 and 142 are closed, causing electrodes 38, 40 to be connected to each other and case 128, thereby dissipating any residual charge on the electrodes. At step 216, switches 140, 142 open and the capacitor starts to charge once again.

The monitoring of the heart 28 resumes at step 200. During the monitoring step, low level cardiac signals, such as the signals associated with fibrillation, are not masked by charges on the electrodes 38, 40 or polarization of the tissues around these electrodes. Therefore, any arrhythmia following a defibrillation shock applied at step 210 can be detected with far less delay and, accordingly, appropriate therapy (steps 206, 208, 210) can be applied earlier and more effectively than in the prior art.

While the invention has been described by means of specific embodiments, it is understood that modifications and variations could be made thereto by those skilled in the art without departing from the spirit and the scope of the invention. It is therefore to be understood that within the scope of the claims, the invention may be practiced otherwise than as specifically described herein.

What is claimed is:

1. An implantable medical device, adapted to selectively generate therapeutic shocks to tissue of a heart through electrodes implanted in the heart, the therapeutic shocks causing a residual electrical charge on the electrodes and polarization of the tissue, comprising:

a pulse generator that generates a short duration pulse;
   an output circuit coupled to the pulse generator and arranged to apply the short duration pulse to the electrodes subsequent to a therapeutic shock to cause the charge to dissipate rapidly, the short duration pulse having a low amplitude to avoid stimulating the tissue of the heart; and
   a switching circuit arranged to selectively short the electrodes together.

2. The implantable medical device of claim 1, wherein the output circuit controls the switching circuit to short the electrodes together after the short duration pulse is applied.

3. The implantable medical device of claim 1, further comprising a case, the switching circuit being further arranged to short the electrodes to the case.

4. The implantable medical device of claim 1, wherein the switching circuit comprises a timing circuit that defines a shorting cycle following the second cycle, the electrodes being shorted together during the shorting cycle.

5. The implantable medical device of claim 1, wherein:
   the electrodes comprise an RV coil electrode, a tip electrode, and a case electrode; and
   the switching circuit comprises a timing circuit that defines a shorting cycle following the second cycle, at least one of the RV coil electrode or the tip electrode being selective shorted to the case electrode during the shorting cycle.

6. The implantable medical device of claim 1, wherein:

the pulse generator generates a multiphasic therapeutic shock having a first polarity pulse followed by a second polarity pulse; and the pulse generator further generates the short duration pulse with a polarity opposite the second polarity pulse.

7. The implantable medical device of claim 1, wherein the electrodes comprise an RV coil electrode, a tip electrode, and a case electrode, further comprising:

an amplifier that senses a voltage generated between the RV coil electrode and the tip electrode; and a control circuit that produces a neutral reference for the amplifier based on the RV coil electrode and the case electrode.

8. The implantable medical device of claim 7, wherein:

the amplifier comprises a first resistor coupled to the RV coil and a second resistor coupled to the case electrode, the first and second resistors being variable; and the control circuit further configured to vary the first and second resistors so as to neutralize the offset voltage produced by the RV coil electrode and the case electrode.

* * * * *